United States Patent
Mielekamp et al.

(10) Patent No.: US 8,050,471 B2
(45) Date of Patent: Nov. 1, 2011

(54) IMAGE PROCESSING SYSTEM AND METHOD FOR DISPLAYING IMAGES DURING INTERVENTIONAL PROCEDURES

(75) Inventors: Pieter Maria Mielekamp, Eindhoven (NL); Robert Johannes Frederik Homan, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1156 days.

(21) Appl. No.: 11/719,551

(22) PCT Filed: Nov. 16, 2005

(86) PCT No.: PCT/IB2005/053774
§ 371 (c)(1),
(2), (4) Date: May 17, 2007

(87) PCT Pub. No.: WO2006/056909
PCT Pub. Date: Jun. 1, 2006

(65) Prior Publication Data
US 2009/0148009 A1   Jun. 11, 2009

(30) Foreign Application Priority Data

Nov. 23, 2004  (EP) .................................... 04105990
Feb. 23, 2005  (EP) .................................... 05101357

(51) Int. Cl.
*G06T 15/00* (2006.01)
(52) U.S. Cl. ...................................... 382/128; 600/424
(58) Field of Classification Search .................. 382/128, 382/131, 132; 600/424
See application file for complete search history.

(56) References Cited

U.S. PATENT DOCUMENTS

| 5,951,475 | A  | * | 9/1999 | Gueziec et al. ............... 600/425 |
| 6,351,513 | B1 |   | 2/2002 | Bani-Hashemi et al. |
| 6,363,134 | B1 | * | 3/2002 | Suzuki ........................... 378/15 |
| 6,404,843 | B1 |   | 6/2002 | Vaillant |
| 6,711,433 | B1 |   | 3/2004 | Geiger et al. |
| 6,798,390 | B1 | * | 9/2004 | Sudo et al. ........................ 345/7 |
| 7,599,730 | B2 | * | 10/2009 | Hunter et al. ................. 600/424 |
| 2002/0045817 | A1 |   | 4/2002 | Ichihashi |

(Continued)

FOREIGN PATENT DOCUMENTS

| WO | WO0068889 A1 | 11/2000 |
| WO | WO2004034329 A2 | 4/2004 |

OTHER PUBLICATIONS

Penney et al. "Validation of a two-to three-dimensional registration algorithm for aligning preoperative CT images and intraoperative fluoroscopy images." Med. Phys. 28(6), Jun. 2001, pp. 1024-1032.*

(Continued)

*Primary Examiner* — Jon Chang

(57) ABSTRACT

To reduce the contrast fluid and X-ray load on patients during interventional procedures, a real-time visualization architecture combines 2D live images with 3D reconstructed volume information. In general, 2D X-ray images are recorded from below (Posterior Anterior) and presented head up (Anterior Posterior) by applying a mirroring operation on the image data. In order to ensure a correct alignment of the 2D live images within the reconstructed 3D volume, the 3D information is displayed under the same inverse viewing angle as the 2D live images by applying a mirroring around the Y-axis to the 3D information and by presenting the 3D information in a reverse sorting order. Furthermore, transparent surface/volume rendering combined with silhouette rendering maintains the contrast in the 2D information while preserving the 3D impression.

12 Claims, 5 Drawing Sheets

U.S. PATENT DOCUMENTS

| | | | |
|---|---|---|---|
| 2003/0181809 A1* | 9/2003 | Hall et al. | 600/425 |
| 2004/0138557 A1 | 7/2004 | Le et al. | |
| 2004/0215071 A1 | 10/2004 | Frank et al. | |
| 2005/0203385 A1* | 9/2005 | Sundar et al. | 600/427 |
| 2006/0078195 A1* | 4/2006 | Vaillant et al. | 382/154 |
| 2006/0079759 A1* | 4/2006 | Vaillant et al. | 600/424 |

OTHER PUBLICATIONS

Weese et al. "2D/3D Registration and Motion Tracking for Surgical Interventions." Philips Journal of Research, vol. 51, No. 2, 1998, pp. 299-316.*

* cited by examiner

IMAGE PROCESSING SYSTEM AND METHOD FOR DISPLAYING IMAGES DURING INTERVENTIONAL PROCEDURES

This invention relates generally to an image processing system and method for enabling visualisation and investigation of internal parts of a live subject by acquiring live, two-dimensional images in respect thereof during an interventional procedure.

The imaging of body volumes and internal parts of a live subject is practiced notably in the field of medical diagnostics and therapy, that is, in the context of X-ray fluoroscopy. Therefore, the X-ray projection of a biological body volume will be considered hereinafter by way of example, but the present invention is not intended to be restricted thereto and can be used in all fields of application with similar secondary conditions.

Referring to FIGS. 1 and 2 of the drawings, a typical X-ray system comprises a swing arm (C-arc or G-arc) 1 supported proximal a patient table 2 by a robotic arm 3. Housed within the swing arm 1, there is provided an X-ray tube 4 and an X-ray detector 5, the X-ray detector 5 being arranged and configured to receive X-rays 6 which have passed through a patient 7 and generate an electrical signal representative of the intensity distribution thereof. By moving the swing arm 1, the X-ray tube 4 and detector 5 can be placed at any desired location and orientation relative to the patient 7.

In the treatment of various types of condition and disease, a special medical application is provided by the fluoroscopic observation of the propagation of a catheter in the vascular system of the patient. Thus, during intervention, a catheter or guidewire is required to be advanced under X-ray surveillance (fluoroscopy), and as accurately as possible, through the vessels to an internal part of interest. While this procedure is performed, the vessel structures are made visible on a first monitor for short periods of time, in the form of two-dimensional live images, by introducing short bursts of a radio-opaque contrast agent through the catheter and obtaining X-ray images using, for example, the system described with reference to FIGS. 1 and 2 of the drawings.

For the safety of the patient, it is highly desirable to minimise the exposure to X-rays and also to minimise the amount of contrast agent introduced into the body, and it is therefore known to display during an intervention, on a second monitor, one or more pre-interventional X-ray images acquired in respect of the area of interest, so as to assist navigation. These pre-interventional images support the orientation for the attendant physician as a "vascular map" or "road map" of the vascular system. In order to improve guidance during, for example, catheter placement, methods have been developed to overlay such roadmap information on the fluoroscopic images obtained during the intervention, as described in, for example, U.S. Pat. No. 7,454,043.

However, it is highly desirable for the physician to be able to visualise in three dimensions, the two-dimensional fluoroscopic image data acquired during an intervention, as this will enable interventional data to be tracked in real time, whilst significantly reducing the contrast fluid and X-ray exposure load on the patient during the interventional procedure.

It is therefore an object of the present invention to provide an image processing system and method which enables live two-dimensional image data captured in respect of a body volume to be displayed relative to three-dimensional volume data.

In accordance with the present invention, there is provided a system for displaying image data acquired during an intervention procedure in respect of a body volume, said system comprising means for receiving three-dimensional image data in respect of said body volume and reconstructing a three-dimensional image of said body volume, means for receiving two-dimensional image data in respect of said body volume acquired during an intervention procedure, means for aligning said two-dimensional image data with a corresponding region of said three-dimensional image of said body volume, and means for displaying said two-dimensional image data within said corresponding region of said three-dimensional image of said body volume.

The three-dimensional image data is preferably acquired prior to the intervention procedure, and the two-dimensional image data is beneficially live and displayed substantially in real-time within the three-dimensional image of the body volume.

The three-dimensional image data is beneficially acquired by means of a 3D rotational scan (preferably wherein a contrast agent is injected into the body volume), particularly since such a scan (e.g 3 DRA) is routinely obtained prior to any intervention for diagnostic and treatment evaluation purposes. The two-dimensional image data may, for example, be acquired by means of X-ray fluoroscopic imaging means.

In conventional 2D (fluoro) image display, the 2D images tend to be mirrored, as a result of which, the images may contain a wrong perspective distortion when displayed within the three dimensional image of the body volume. Thus, in a preferred embodiment, mirroring is applied to the three-dimensional image data, preferably around the Y (vertical) axis, and the 3D image data is beneficially presented for display in an inverse sorting order relative to the depth of the 3D image of the body volume.

Beneficially, the live two-dimensional image data is displayed within a silhouette rendering of the three-dimensional image data so as to provide minimal obstruction/observation of the live two-dimensional image data. In some cases it may be further beneficial to combine transparent surface/volume rendering of said three-dimensional image data with the silhouette rendering thereof.

Preferably, live two-dimensional image data is superimposed on the three-dimensional image data only where two-dimensional image data is present. This may be achieved using blending means, wherein the two-dimensional pixel density is used as a blending factor.

Also in accordance with the present invention, there is provided a method of displaying image data acquired during an intervention procedure in respect of a body volume, the method comprising acquiring three-dimensional image data in respect of said body volume and reconstructing a three-dimensional image of said body volume, acquiring during said intervention procedure two-dimensional image data in respect of said body volume, aligning the two-dimensional image data with a corresponding region of the three-dimensional image of the body volume, and displaying said two-dimensional image data within said corresponding region of said three-dimensional image of said body volume.

These and other aspects of the present invention will be apparent from, and elucidated with reference to, the embodiment described herein.

An embodiment of the present invention will now be described by way of example only and with reference to the accompanying drawings, in which.

Prior to the intervention, a 3D rotational scan is acquired, reconstructed and prepared for visualisation. During the actual intervention, live 2D (fluoro) images are acquired, processed and visualised in combination with the 3D volumes.

In order to give the correct visual impression the incoming live 2D information must be positioned into the 3D-viewing pyramid and carefully lined up with the 3D-volume information.

In order to position the 2D data in 3-space, the geometry information as used during the 2D acquisition is passed to the viewing control. By using this geometry information a matching virtual camera set-up; i.e. viewing pyramid and line of side, can be used for 3D visualisation.

As mentioned before due to the preferred presentation mode the 2D images are mirrored. As a result the images contain a wrong perspective distortion when positioned in 3-space. The 2D information itself can however not be re-warped due to lack of depth information. So the approach that is taken is to display the 3D information under the same inverse viewing projection as dictated by the 2D imaging. Due to the nature of homogeneous coordinates it is not possible to define the desired inverse viewing pyramid by a modification of the perspective projection transformation, that is part of the graphics pipeline.

The solution is to apply a mirroring around the Y-axis and present the 3D information in back to front sorting order.

The above-mentioned mirroring may, for example, be accomplished by inverting all x-coordinates, which can (in OpenGL) be defined by a glScale(−1,1,1) operation. For the 3D texture map-based volume rendering, where the sorting is explicit this can be simply accomplished by a re-ordering of the textured slices through the viewing volume.

For 3D surface rendering the inverse sorting ordering can be accomplished by changing the default hidden surface Z-buffer test. Again, in OpenGL, this can be specified using the glDepthFunction, that compares the incoming value with the depth value present in the depth buffer, so that pixels further away overwrite nearby pixels.

Due to the mirror operation, the notion of front/facing polygons will be inverted which influences the lighting calculations. This inversion can be tackled by changing the orientation of the ordered vertices of the projected polygons from the default counter clockwise to a clockwise orientation.

In order to keep the contrast in the 2D information while preserving the 3D-volume impression special measures have to be taken for visualisation.

Figure 1:
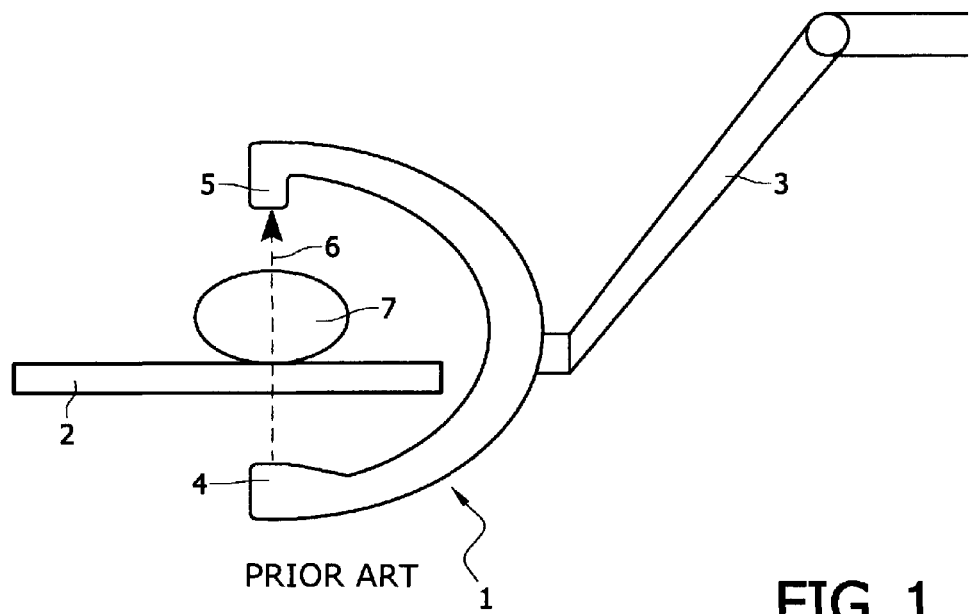
FIG. 1 is a schematic side view of an X-ray swing arm.
Figure 2:
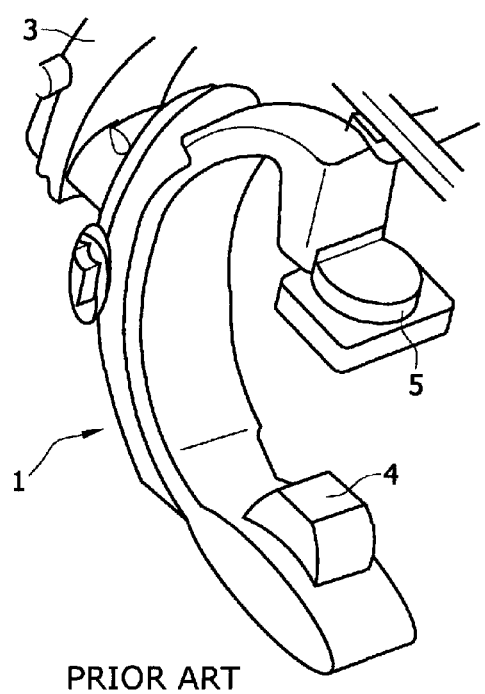
FIG. 2 is a perspective view of an X-ray swing arm.
Figure 3A:
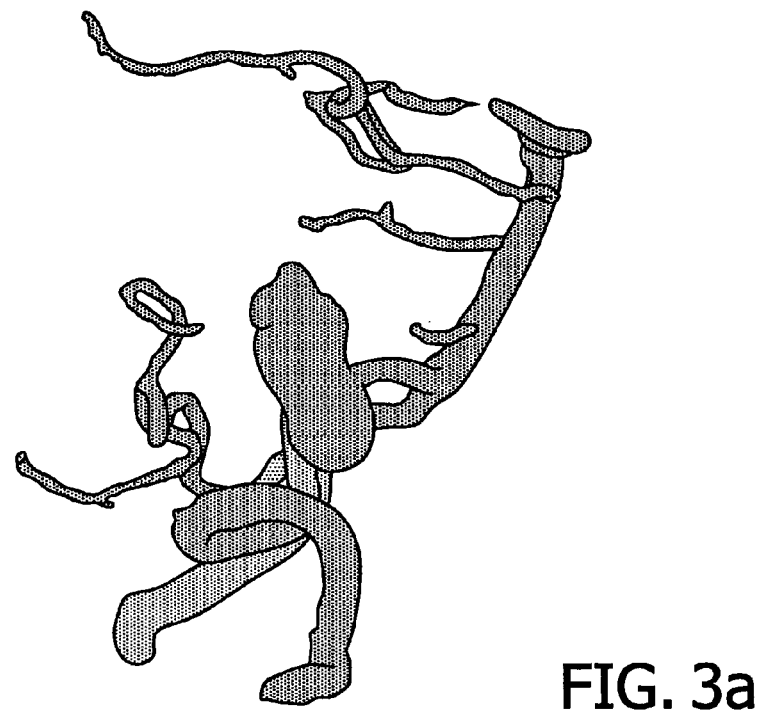
FIGS. 3a and 3b are respective surface and silhouette renderings of an aneurysm.
Figure 3B:
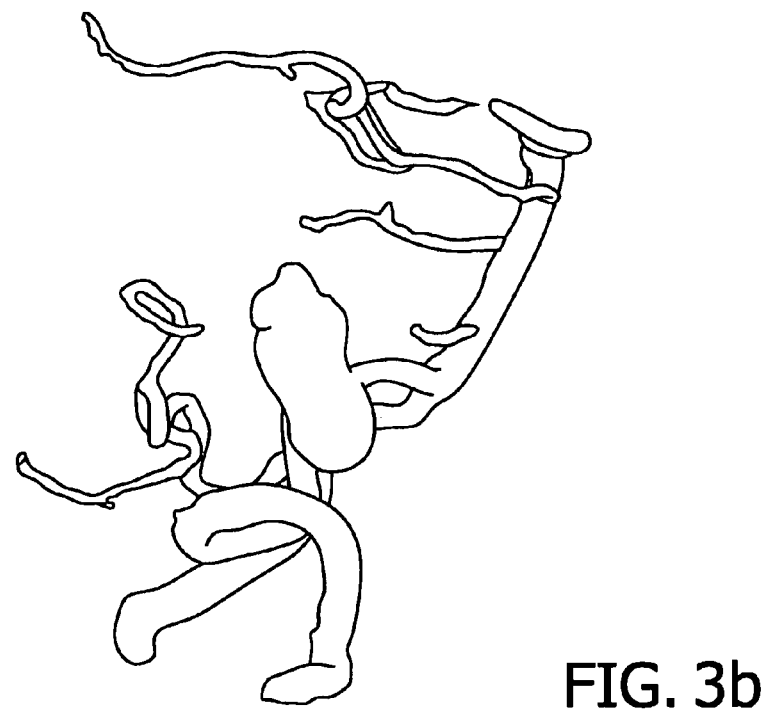

Silhouette renderings are useful to effectively convey a great deal of information, such as the structure of a volume model, with a few strokes (see FIG. 3*b*, which is a silhouette rendering of an aneurysm, compared with the surface rendering thereof shown in FIG. 3*a*). For polygonal meshes, the silhouette edges consist of visible segments of all edges that connect back-facing polygon to front-facing polygons. By combining silhouettes to render the volume data with the live 2D data, a great deal of the volume information can be still conveyed, while this rendering method provides minimal obstruction for the live data. Especially within an interactive viewing context, where a lot of 3D information is coming from the hidden line elimination, this proves to be effective.

However in the context of interventional radiology where the 3D models will be inspected less interactively and the orientation is dictated by the live 2D acquisition a lot of the "shape from shading information", as provided by the physics based volumes/surface rendering, is missing. On the other hand when combining volumes/surface rendering with live 2D images the intended goal of keeping contrast in the 2D information is lost.

It is proposed herein to make a combination of both methods by using transparent surface/volume rendering in combination with silhouette rendering. By selecting the amount of transparency an optimal setting of the conflicting requirements of maintaining contrast in the 2D information while preserving the 3D-volume impression can be user controlled. To combine the 2D information with the 3D volumes, live data is superimposed on top of the 3D information, but only where 2D data is actually present By using the blending hardware this can be done at the pixel level by using the 2D-pixel density as blending factor.

An observation that can be made is that the clinically interesting interventional data is contained within the vessel lumen. So it is highly beneficial to display the 2D information inside and blank out the information outside the vessel volume. By using the hardware stencil buffer the area outside (or inside) the irregular shaped projected vessel data can be masked out on the fly. Non interesting parts of the vessel tree can also be cut-way manually.

On the other hand, the volume data can also be enriched for instance by colour coding aneurysms or by virtually placing stents, markers etc.

In order to perform the compositing visualisation in real time it is proposed to make optimal use of known graphical hardware. By using texture-mapping hardware zooming and panning can be done on the 2D/3D image compositions, as will be apparent to a person skilled in the art. By using hardware supported lookup tables, the convolution kernels, window width/level and image enhance functions can operate on standard graphics hardware.

An observation that can be made is that 3D information will only be redisplayed when the 2D geometry parameters are changed or when the 3D-visualisation parameters are modified. So during the live 2D acquisition the 3D information as contained in the Colour and Stencil buffers can be buffered and re-used.

Figure 4:
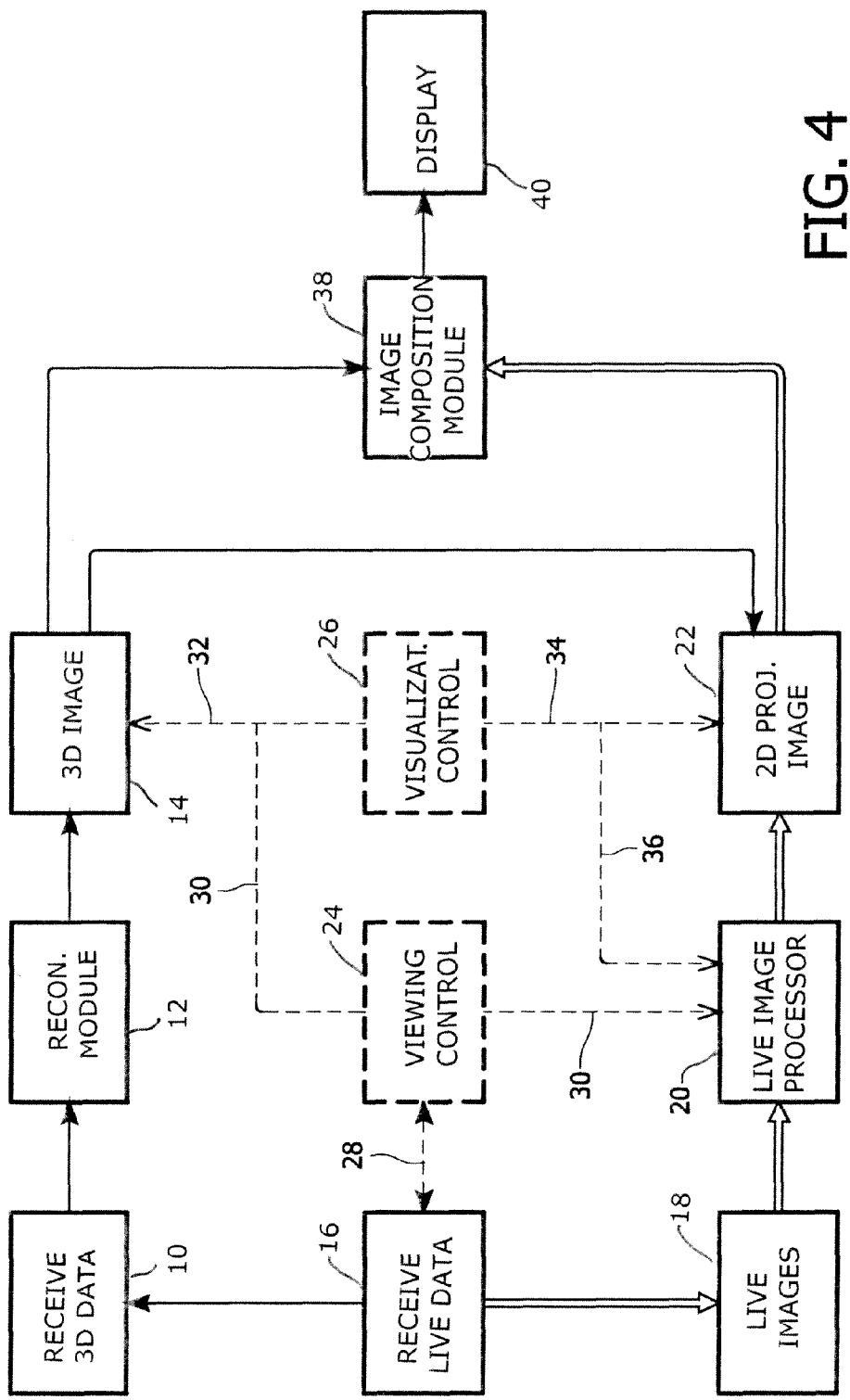
FIG. 4 is a schematic block diagram illustrating the principal features of an image display system according to an exemplary embodiment of the present invention.

A schematic overview of the proposed visualisation process is shown in FIG. 4.

Referring to FIG. 4 of the drawings, an image display system according to an exemplary embodiment of the present invention comprises means 10 for receiving three-dimensional image data representative of a body volume, which image data is acquired by, for example, a 3 DRA (rotational angiography) technique. This image data is reconstructed at module 12, and a three-dimensional image of the body volume is displayed (at module 14). Means 16 are also provided for receiving live, two-dimensional image data in respect of the body volume acquired, for example, by means of X-ray fluoroscopy techniques as a surgical instrument is moved through the body volume. The live images produced (denoted at block 18) are fed to two-dimensional image processing means 20 and masking means 22 may be used to crop the live images so as to just leave the portion of the image that is of interest (i.e. the end of the surgical instrument). Control means, comprising a viewing control module 24 and a visualisation control module 26. Geometry information, based on the geometric settings of the acquisition system during the live 2D acquisition, is fed to the viewing control module 24, and windowing, zooming and viewing control signals 30 also based on the settings of the 2D acquisition system are fed to the 3D display module 14 and the two-dimensional image processing means 20. The visualisation control module 26 is arranged to generate a control signal 32 identifying the rendering made and representative of transparency control according to user settings and parameters. The visualisation control module 26 is also arranged to generate a signal 34 representative of the degree of cropping or masking required to be performed by the module 34 and a signal 36, derived therefrom, is also fed to the two-dimensional image processing means 20 to effect edge enhancement and noise reduction. 3D image data from the module 14 and 2D image data from the module 22 are fed to an image composition module 38, which is arranged to align the image of interest with the corresponding region of the 3D body volume, and the resultant image, of the live 2D image data of interest within the 3D body volume is displayed at 40. Thus, based on the geometrical settings of the acquisition system during the live acquisition 2D image data, a matching 3D view is created within which the 2D image data is displayed. It will be appreciated that in the diagram of FIG. 4, the thick connecting lines denote 2D image data, the thinner connecting lines denote 3D image data, and the broken lines denote control data.

In a different configuration of the system, the 2D images may have been pre-processed and or stored and can be re-played and presented in combination with and relative to the volume data. The 3D visualisation can also be done on the basis of CT or other volume data, which has been registered with the rotational x-ray data.

A process according to an exemplary embodiment of the present invention will now be illustrated by means of a radiated light bulb.

Figure 5:
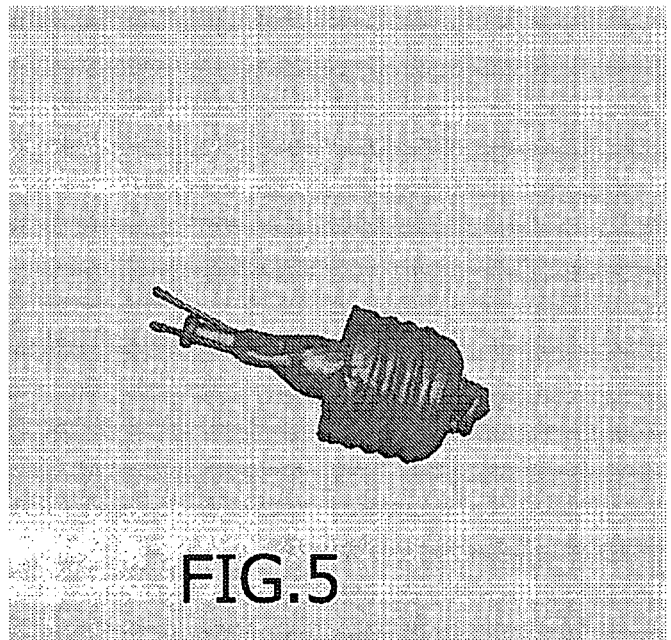
FIGS. 5 to 8 are schematic diagrams provided to illustrate by means of a radiated light bulb, a 3D visualisation process according to an exemplary embodiment of the present invention.
Figure 6:
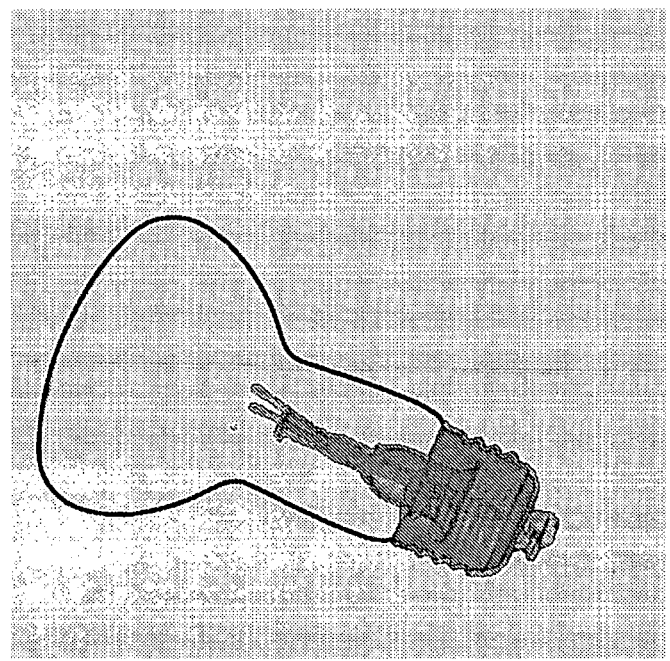
Figures 7, 8:
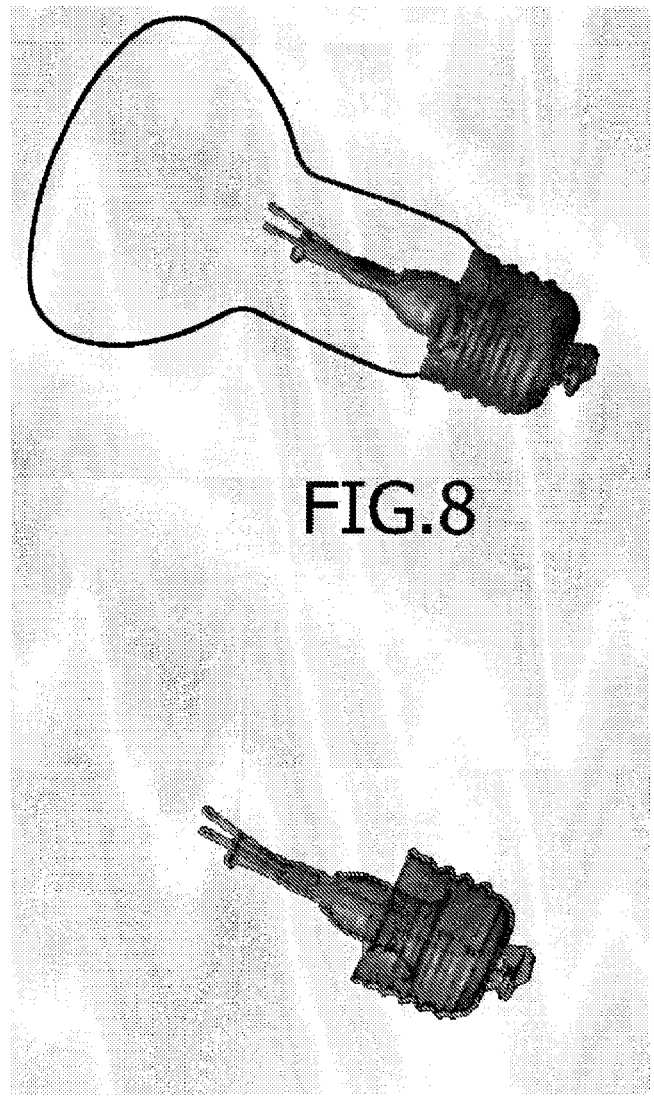

FIG. 5 shows the surface rendered 3D volume. FIG. 6 shows a 2D live data image. FIG. 7 illustrates the effect of the cropping operation on the 2D image to eliminate distracting or irrelevant information. FIG. 8 shows the aligned composition of both 2D and 3D images after edge enhancement and blending control.

In summary, to reduce the contrast fluid and x-ray load on patients during interventional procedures, the present invention provides a real time visualization architecture to combine 2D live images with 3D reconstructed volume information.

Generally 2D x-ray images are recorded from below (Posterior Anterior) and presented head up (Anterior Posterior) by applying a mirroring operation on the image data. To ensure a correct alignment of the 2D live images within the reconstructed 3D volume the invention suggests to display the 3D information under the same inverse viewing angle as the 2D live images by applying a mirroring around the Y-axis to the 3D information and by presenting the 3D information in a back to front sorting order. Furthermore in a preferred embodiment of the invention it is proposed to combine transparent surface/volume rendering with silhouette rendering to maintain the contrast in the 2D information while preserving the 3D impression. In this way an optimal setting of the conflicting requirements of maintaining contrast in the 2D information while preserving the 3D impression can be user controlled by selecting the amount of transparency. Other essential features of the invention are a reduction of irrelevant data by only displaying the 2D information within the vessel volume and a real time visualization of the 2D/3D image compositions by optimal usage of the graphical hardware.

With regard to the inverse projection geometry the following additional remarks are made. In order to reduce stray-radiation, the x-ray source is kept under the patient-table during intervention. Since patients are normally lying face-up on a table and clinicians conventionally work with a frontal view presentation, the 2D x-ray images will generally be subjected to a substantial inverse perspective distortion, as described above. In a preferred embodiment of the present invention, the same inverse projection is acquired in the volume image by observing the volume model from the opposite side with the appropriate virtual camera settings. Then the projection image is constructed from back-side to front-side in a way that visual elements which are located at the front-side are positioned at the back-side, and vice versa.

Thus, interventional image data, such as the position of a guide wire within the blood vessels of a patient can be tracked using the system and method of the above-described preferred embodiment of the present invention, whereby incoming 3D X-ray image data can be properly aligned with the 3D volume data, contrast in the 2D information can be maintained whilst preserving the 3D-volume impression, the amount of distracting and/or irrelevant information can be reduced, and the visualisation can be performed in real-time.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for displaying image data acquired during an intervention procedure in respect of a body volume, said system comprising:

a reconstruction module which reconstructs a three-dimensional surface rendering image of vasculature in said body volume from three-dimensional image data; and generates a three-dimensional silhouette image of the vasculature in the body volume;

a processor which generates a series of two-dimensional images of the vasculature and an interventional instrument in said body volume during an intervention procedure;

a visualization control which crops portions of the two-dimensional image which are remote from a tip of the interventional instrument;

an image compensation module which aligns and superimposes said two-dimensional cropped image with a corresponding region of said three-dimensional silhouette image of the vasculature in said body volume; and a display on which said cropped two-dimensional image is displayed within said corresponding region of said three-dimensional silhouette image of the vasculature of said body volume.

2. The system according to claim 1, wherein three-dimensional image data for reconstruction into the three-dimensional image of the vasculature is acquired prior to the intervention procedure, and the data for the two-dimensional image is acquired live and is displayed substantially in real-time within the three-dimensional image of the vasculature of the body volume during the interventional procedure.

3. The system according to claim 2, further including:
a 3D rotational scanner which generates the three-dimensional image data.

4. The system according to claim 1, further including:
an X-ray fluoroscopic imager which generates the two-dimensional images.

5. The system according to claim 1, wherein the two-dimensional image is a projection image projected from below the body volume upward such that a posterior portion of the body volume is in front to an anterior portion of the body volume and the reconstruction module reconstructs the three-dimensional image with the anterior portion of the body volume in front of the posterior portion of the body volume and the reconstruction module further mirrors the three-dimensional image to move the posterior portion of the body volume in front of the anterior portion of the body volume.

6. The system according to claim 5, wherein said three-dimensional image is presented for display in an inverse sorting order relative to a depth of the three-dimensional image of the body volume.

7. The system according to claim 1, wherein the visualization control under user control, selects a degree of transparency of the vasculature in the surface rendering image, the reconstruction module being controlled by the visibility control to combine the surface rendering image with an intensity corresponding to the selected degree of transparency with the three-dimensional silhouette image.

8. The system according to claim 1, wherein the visualization control crops said two-dimensional image to remove all of the vasculature such that the two-dimensional image that is superimposed on the three-dimensional silhouette image depicts only the tip of the intervention instrument.

9. A method of displaying image data acquired during an intervention procedure in respect of a body volume, the method comprising:
acquiring three-dimensional image data of vasculature in said body volume;
reconstructing the three-dimensional image data into a surface rendering image of the vasculature in said body volume;
generating a silhouette image of the vasculature from the three-dimensional image data;
acquiring during said intervention procedure a series of two-dimensional projection images of said body volume including at least a tip of an interventional instrument used in the interventional procedure;
adjusting a degree of transparency of the surface rendering image of the vasculature and combining the surface rendering image with the silhouette image;
aligning and combining each two-dimensional projection image with a corresponding region of the combined surface rendering and silhouette images of the vasculature in the body volume; and
displaying each two-dimensional projection image within said corresponding region of said combined surface rendering and silhouette images of the vasculature of said body volume.

10. The method according to claim 9, wherein acquiring the two-dimensional projection images includes projecting x-rays from a posterior side of the body volume through the body volume and receiving x-rays that have traversed the body volume with a detector such that in the two-dimensional projection image posterior portions of the body volume are in front of anterior regions of the body volume, and further including:
mirroring the three-dimensional surface rendering and silhouette images such that the posterior portions of the body volume are in front of the anterior portions of the body volume.

11. A system for displaying image data during an interventional procedure in a body volume, the system comprising:
a reconstruction module which reconstructs 3D image data into a 3D image of the body volume, in the 3D image, an anterior portion of the body volume being in front of a posterior portion of the body volume;
an x-ray imager which has an x-ray source disposed on a posterior side of the body volume and an x-ray detector disposed on an anterior side of the body volume, the x-ray imager projecting radiation from the x-ray source through the body volume to generate a 2D image in which the posterior portion of the body volume is in front of the anterior portion of the body volume;
the reconstruction module further mirrors the 3D image such that in the mirrored 3D image, the posterior portions of the body volume are in front of the anterior portions of the body volume;
an image composition module which aligns and combines the mirrored 3D image and the 2D image; and
a display on which the aligned and combined mirrored 3D image and 2D image are displayed.

12. The system according to claim 11, wherein the reconstruction module is further configured to generate a surface rendering image and a silhouette image from the 3D image data and align and combine the surface rendering and silhouette images, and further including:
a visualization control by which a user selects a degree of transparency of the surface rendering image, the combined surface rendering image with the selected degree of transparency and the silhouette image being aligned and combined with the 2D image by the image composition module.

* * * * *